United States Patent [19]
Bharucha et al.

[11] 3,932,512
[45] Jan. 13, 1976

[54] ANTIVIRAL 1,2,3,4-TETRAHYDRO-1,-ALKANO NAPHTHALENAMINE DERIVATIVES

[75] Inventors: Kekhusroo R. Bharucha, Toronto; Djordje Ajdukovic, Montreal; Vytautas Pavilanis, Westmount; Angus Campbell Mackay, Toronto, all of Canada

[73] Assignee: Canada Packers Limited, Toronto, Canada

[22] Filed: Sept. 14, 1972

[21] Appl. No.: 289,122

[52] U.S. Cl. ........ 260/570.9; 260/349; 260/453 PR; 260/501.1; 260/501.12; 260/514 G; 260/515 A; 260/546; 260/562 R; 260/566 A; 260/570.5 P; 260/576; 260/577; 260/578; 260/586; 260/590; 424/316; 424/330
[51] Int. Cl.²................................... C07C 87/29
[58] Field of Search......... 260/570.8, 577, 570.9 R, 260/576, 578; 424/330

[56] References Cited
FOREIGN PATENTS OR APPLICATIONS
41-18944  1/1966  Japan................................ 260/570.9

OTHER PUBLICATIONS
Kitahonoki et al., "Tetrahedron", Vol. 24, pp. 4605 – 4623, (1968).

*Primary Examiner*—R. V. Hines
*Attorney, Agent, or Firm*—Bacon & Thomas

[57] ABSTRACT

Amine derivatives of 1,2,3,4-tetrahydro-1,4-alkanonaphthalenes, and the use of such compounds to control viral infections, particularly influenza viruses, in warm-blooded animals are disclosed. Pharmaceutical compositions containing an effective amount of the novel compounds and a pharmaceutically acceptable carrier are also disclosed.

6 Claims, No Drawings

ANTIVIRAL 1,2,3,4-TETRAHYDRO-1,-ALKANO NAPHTHALENAMINE DERIVATIVES

The present invention relates to 1,2,3,4-tetrahydro-1,4-alkanonaphthalenamine derivatives and to the production and use thereof. In one aspect, the invention relates to new chemical compounds of the general formulas:

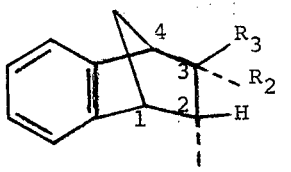

and

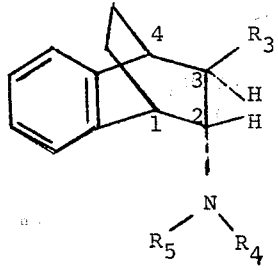

and their non-toxic pharmaceutically acceptable acid addition salts wherein:

$R_1$ is hydrogen $R_2$ either hydrogen or lower alkyl from 1 to 6 carbon atoms $R_3$ is selected from the group consisting of hydrogen, amino, alkyl substituted amino from 1 to 6 carbon atoms, dialkylaminoalkyl wherein alkyl contains 1 to 6 carbon atoms or phenyl and $R_4$ and $R_5$ are selected from the group consisting of hydrogen, or lower alkyl from 1 to 6 carbon atoms except that when $R_3$ is hydrogen, neither of $R_4$ and $R_5$ is methyl.

It is an object of the present invention to provide new anti-viral agents of the class of compounds having the formulas given above.

Another object of the invention is to provide a process for preparing 1,2,3,4-tetrahydro-1,4-alkanonaphthalenamine compounds having the specified formulas.

A further object of the invention is to provide pharmaceutical compositions containing an effective anti-viral amount of a compound of the class of 1,2,3,4-tetrahydro-1,4-alkanonaphthalenamine compounds described hereinbelow. These and other objects will be apparent from the subsequent description to those skilled in the art to which the present invention pertains.

There are relatively few known compounds that have significant anti-viral activity against influenza viruses. One of these generally recognized as having prophylactic activity against these viruses is the hydrochloride of amantadine. Other compounds reported to have activity against influenza viruses are disclosed in U.S. Pat. Nos. 3,483,254, 3,496,228, 3,538,160, 3,534,084 and 3,592,934.

According to the invention, there has been discovered a further class of compounds having pharmaceutical application and utility as anti-influenza agents. The compounds are characterized by low-toxicity combined with good activity against influenza viruses, particularly influenza virus $A_2$, as shown by standard tissue culture tests and by in vivo tests in mice.

It should be understood that the compounds within the scope of the above structural formulae, having a basic amino group or diamino groups, readily form acid addition salts and such salts having a non-toxic anion are also included within the scope of the present invention.

Representative of such salts are the hydrochlorides, hydrobromides, sulfates, phosphates, acetates, succinates, adipates, propionates, tartrates, citrates, bicarbonates, pamoates, cyclohexylsulfamates, and acetylsalicylates.

Particularly preferred anti-viral agents are the hydrochlorides of the following compounds:

I. 1,2,3,4,-tetrahydro-1,4-methanonaphthalen-endo-2-amine;

II. 1,2,3,4-tetrahydro-1,4-methanonaphthalen-endo-2-methylamine;

III. 1,2,3,4-tetrahydro-1,4-methanonaphthalen-exo-3-dimethylaminomethyl-endo-2-amine;

IV. 1,2,3,4-tetrahydro-1,4-methanonaphthalen-endo-3-methyl-endo-2-amine;

V. 1,2,3,4-tetrahydro-1,4-methanonaphthalen-exo-3-endo-2-diamine;

VI. 1,2,3,4-tetrahydro-1,4-methanonaphthalen-exo-3-phenyl-endo-2-amine; and

VII. 1,2,3,4-tetrahydro-1,4-ethanonaphthalen-exo-3-endo-2-diamine.

The general procedure for preparing compounds I, II, III, and IV, listed above, is illustrated as follows:

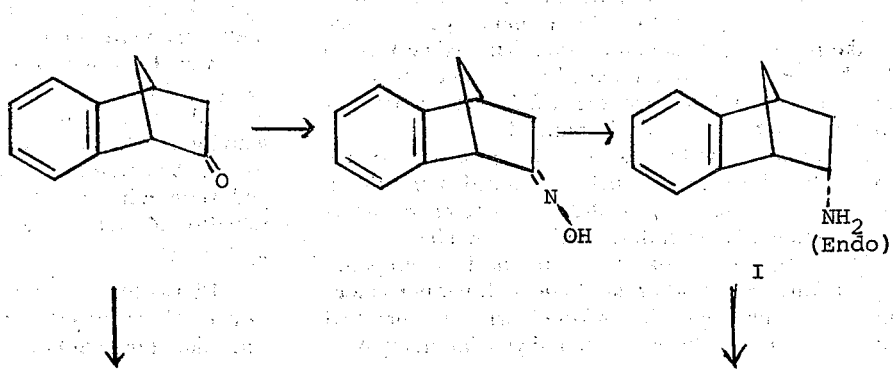

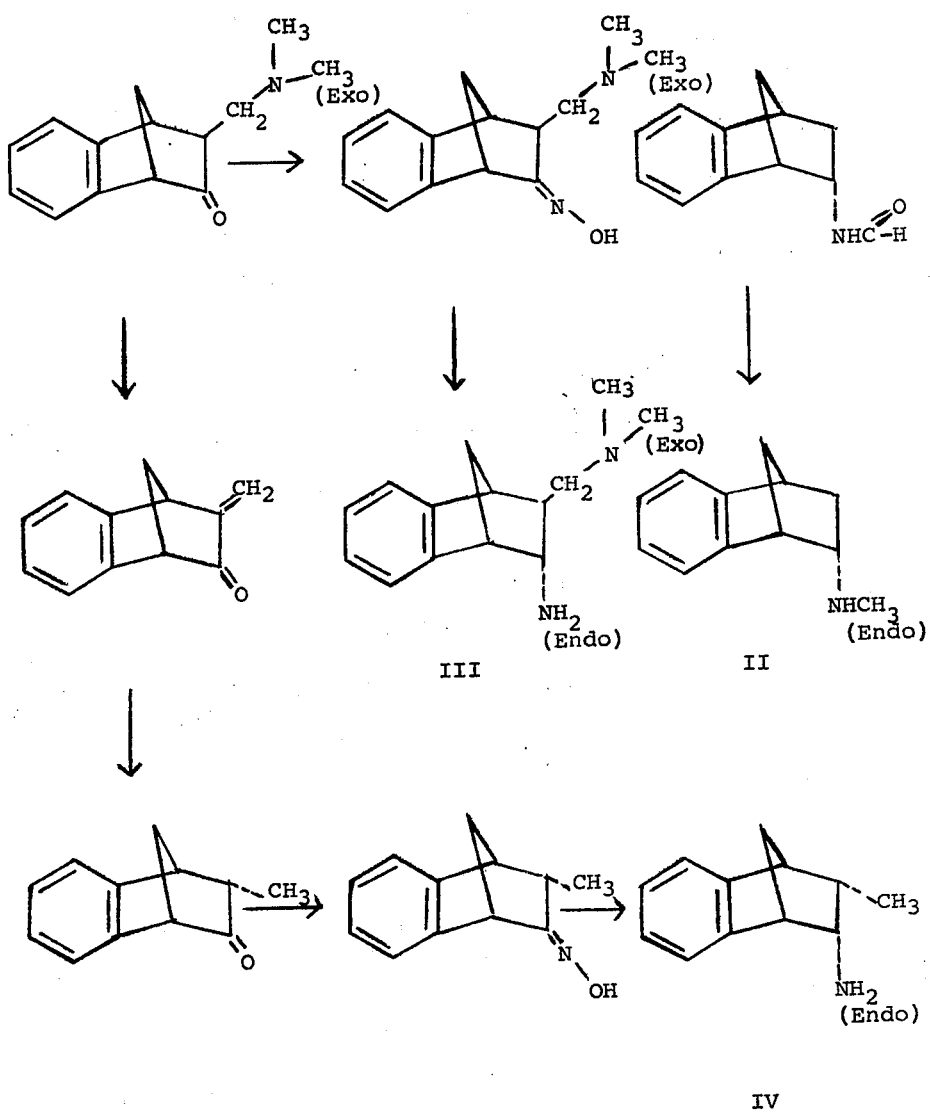

The starting material for the three synthetic schemes outlined above is the benzonorbornen-2-one, which is produced by the reactions of benzonorbornadiene (1,4-dihydro-1,4-methanonaphthalene) with formic acid followed by oxidation of the exo-2-formate with a solution of chromic acid. The preferential exo attack by the formic acid on the benzonorbornadiene is well established in these types of compounds.

The compound of structural formula I is prepared by reacting the ketone with hydroxylamine hydrochloride in the presence of sodium acetate. The oxime formed by the previous step is reduced with sodium metal in absolute ethanol to give the 1,2,3,4-tetrahydro-1,4-methanonaphthalen-endo-2-amine (I).

Compound I can be reacted with formic acid to give the endo-2-formamide which is reduced with lithium aluminum hydride to give the 1,2,3,4-tetrahydro-1,4-methanonaphthalen-endo-2-methylamine (II).

The compound of structural formula III is prepared by reacting benzonorbornen-2-one with paraformaldehyde and dimethylamine hydrochloride in dimethyl formamide to give the exo-3-dimethylaminomethylbenzonorbornen-2-one hydrochloride, which is reacted with hydroxylamine hydrochloride and sodium acetate to give the corresponding oxime. The oxime is converted to the 1,2,3,4-tetrahydro-1,4-methanonaphthalen-exo-3-dimethylaminomethyl-endo-2-amine (III) by reduction with sodium in dry ethanol.

An intermediate in the synthesis of compound III, the exo-3-dimethylaminomethylbenzonorbornen-2-one hydrochloride, is heated at 250°C to give 3-methylenebenzonorbornen-2-one. The 3-methylenebenzonorbornen-2-one is hydrogenated using a Pd/C catalyst in ethyl acetate. The endo-3-methylbenzonorbornen-2-one thus produced is reacted with hydroxylamine hydrochloride and sodium acetate to give the keto-oxime. As before, the oxime is reacted with sodium in absolute ethanol to give the 1,2,3,4-tetrahydro-1,4-methanonaphthalen-endo-3-methyl-endo-2-amine (IV).

A Diels-Alder reaction is employed to produce compounds V and VI listed above. The scheme below outlines the approach taken in the synthetic work:

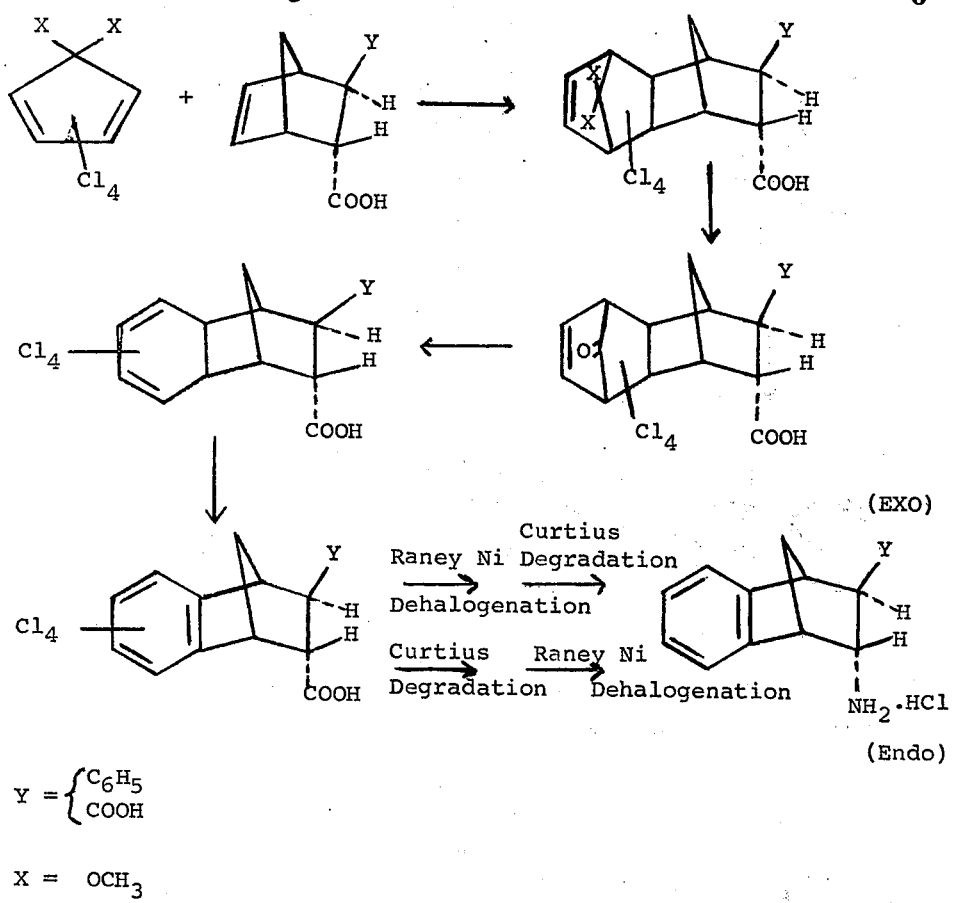

$$Y = \begin{cases} C_6H_5 \\ COOH \end{cases}$$

$$X = OCH_3$$

The production of compounds V and VI begins with the Diels-Alder reaction between norborn-5-ene-trans-2,3-dicarboxylic acid and exo-3-phenylnorborn-5-ene-endo-2-carboxylic acid, respectively, with 5,5-dimethoxytetrachlorocyclopentadiene. The Diels-Alder adducts are then treated with concentrated $H_2SO_4$ and the resulting products are heated in o-dichlorobenzene. This gives 5,6,7,8-tetrachloro-1,2,3,4,5a,8a-hexahydro-1,4-methanonaphthalen-trans-2,3-dicarboxylic acid and 5,6,7,8-tetrachloro-1,2,3,4,5a,8a-hexahydro-1,4-methanonaphthalen-exo-3-phenyl-endo-2-carboxylic acid, respectively. These products are next reacted with bromine in acetic acid to give the corresponding 5,6,7,8-tetrachloro-1,2,3,4-tetrahydro-1,4-methanonaphthalene derivatives which are dehalogenated with Raney nickel and transformed into the desired amines by a Curtius degradation reaction.

Compound VII is produced by still another synthetic method which is illustrated below:

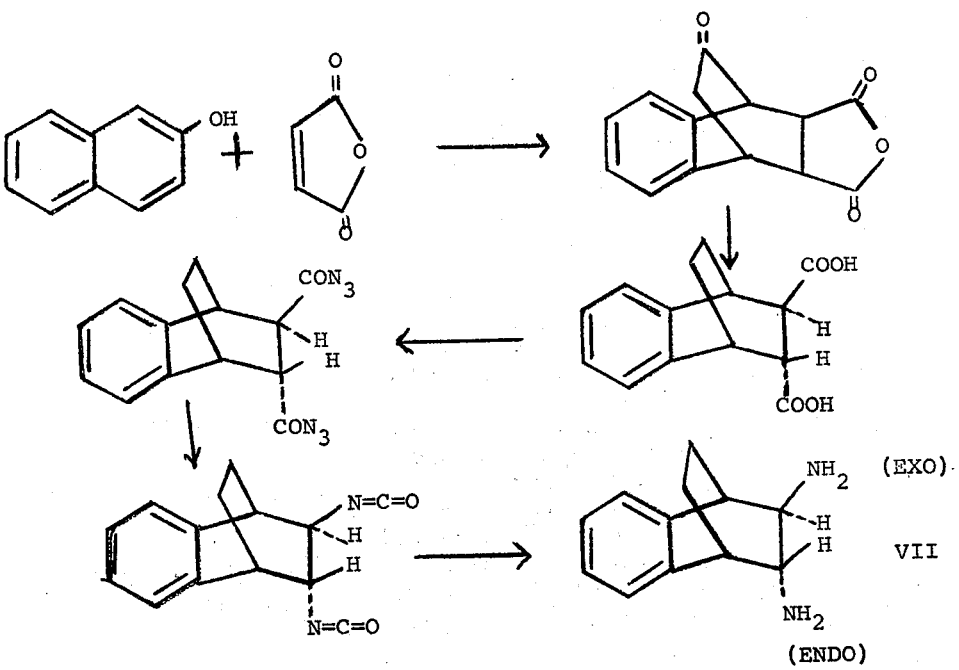

The anhydride produced by Diels-Alder reaction of 2-naphthol and maleic anhydride is reduced under Wolff-Kishner conditions giving benzobicyclo[2.2.2]octene-endo-2-exo-3-dicarboxylic acid. This di-acid is subjected to a Curtius degradation to give the 1,2,3,4-tetrahydro-1,4-ethanonaphthalen-exo-3-endo-2-diamine, VII.

Related compounds which fall within the scope of the instant invention may be prepared by similar methods.

The invention will be further understood by reference to the following illustrative examples:

EXAMPLE 1

Preparation of 1,2,3,4-tetrahydro-1,4-methanonaphthalen-endo-2-amine (I).

Benzonorbornen-2-one [Cook et al, J. Org. Chem., 31,14 (1966)] (1g.) was added to a solution of hydroxylamine hydrochloride (1.25g.) and sodium acetate (1.5g.) in water (5ml). Sufficient ethanol was then added to give a clear solution. This reaction mixture was heated on a water bath for 15 minutes and then shaken until a white solid (1.2g., 100%) precipitated. This material was filtered off and purified by crystallization from chloroform - light petroleum. The material was analyzed by infra-red, nuclear magnetic resonance and elemental analysis techniques and determined to be benzonorbornen-2-one oxime, $C_{11}H_{11}ON$ (m.p. 115°-116°C).

A solution of benzonorbornen-2-one oxime (2g.) in absolute ethanol (120ml.) was heated to reflux under nitrogen and sodium metal (12 g.) was added in small portions with continuous stirring. The reaction mixture was then refluxed for 30 minutes. This viscous suspension was then cooled to room temperature, 100 ml. of water added and the reaction mixture agitated until a clear solution was obtained. This was extracted with ether and the ether extract worked up to give an oil which was dissolved in chloroform and extracted with 10% HCl solution. Removal of water and excess HCl under vacuum from this extract gave a white solid (1g., 40%). The white solid was analyzed by infra-red, nuclear magnetic resonance and elemental analysis techniques and was determined to be the 1,2,3,4-tetrahydro-1,4-methanonaphthalen-endo-2-amine hydrochloride, $C_{11}H_{14}NCl$ (m.p. 230°-231°C). Basification of a sample of this material with 10% NaOH gave, on ether extraction, the required amine as a pale yellow oil which was also analyzed by infra-red, and nuclear magnetic resonance techniques, and the empirical formula was determined to be $C_{11}H_{13}N$.

EXAMPLE 2

Preparation of 1,2,3,4-tetrahydro-1,4-methanonaphthalen-endo-2-methylamine (II).

1,2,3,4-tetrahydro-1,4-methanonaphthalen-endo-2-amine (1.6g.), synthesized by the above process, was mixed with formic acid (1.5g.) and toluene (50 ml.) and heated at reflux for three hours. Evaporation of the solvents yielded a viscous oil which on standing crystallized. Recrystallization from benzene/hexane gave colorless granules which upon spectral analysis were determined to be 1,2,3,4-tetrahydro-1,4-methanonaphthalen-endo-2-formamide $C_{12}H_{13}NO$ (m.p. 88.5°-90°C).

1,2,3,4-tetrahydro-1,4-methanonaphthalen-endo-2-formamide (1.0 g.) was dissolved in dry ether (20 ml.) with sufficient dry dimethoxyethane to complete solution. Lithium aluminum hydride (0.5 g.) was added and the mixture heated at reflux overnight. Work up was accomplished in the usual way by addition of dilute NaOH to the reaction mixture, followed by filtration and washing of the residue with ether. The organic layer was then extracted with dilute HCl and discarded. The aqueous layer was washed with ether, and then treated with concentrated NaOH to free the amine. This was isolated, by extraction with ether, as a mobile oil. It was not characterized as such, but the p.m.r. spectrum shows the presence of an N-methyl group. Conversion to the hydrochloride was effected with concentrated HCl in methanol. Removal of solvents and crystallization gave a pale cream colored solid (600 mg., 46%). The cream colored solid was analyzed by infra-red, nuclear magnetic resonance, and elemental analysis techniques, and was determined to be the 1,2,3,4-tetrahydro-1,4-methanonaphthalene-endo-2-methylamine hydrochloride, $C_{12}H_{16}ClN$ (m.p. 226°-29°C, decomposes).

A similar reaction scheme may be followed employing acetic anhydride in place of formic acid to give the corresponding acetamide which is reduced with "Redal" to give 1,2,3,4-tetrahydro-1,4-methanonaphthalen-endo-2-ethylamine.

EXAMPLE 3

Preparation of 1,2,3,4-tetrahydro-1,4-methanonaphthalen-exo-3-dimethylaminomethyl-endo-2-amine (III).

A solution of benzonorbornen-2-one (0.73 g.), paraformaldehyde (0.3 g.) and dimethylamine hydrochloride (0.82 g.) in distilled DMF (10 ml.) was heated on the steam bath, protected from moisture, overnight (22 hours). Evaporation of the solvent at 65°- 70° (bath temperature) in vacuo left a beige solid (1.97 g.). A $NaHCO_3$ solution and $CH_2Cl_2$ were then added, the organic layer was separated, and the aqueous layer extracted twice with $CH_2Cl_2$. The combined organic extracts were backwashed once with water, dried ($Na_2SO_4$) and evaporated in vacuo to leave a yellow oil (0.89 g.). The hydrochloride was prepared by bubbling HCl gas through a solution of the oil in absolute ethanol (5 ml.) for 5 minutes. Evaporation in vacuo gave a brown solid (0.93 g., m.p. 189°-207°C), which upon crystallization from ethanol/ether furnished a colorless solid (0.55 g., m.p. 211°C). Infra-red and elemental analysis of a sample (73 mg.), which was recrystallized as above to give the pure hydrochloride as a colorless solid (64 mg.), were used to determine the empirical formula of the solid to be $C_{14}H_{18}NOCl$ (m.p. 215°C).

A solution of the 3-exo-dimethylaminomethylbenzonorbornen-2-one hydrochloride, thus prepared, (0.5 g.), hydroxylamine hydrochloride (0.17 g.) and fused anhydrous sodium acetate (0.4g.) in absolute ethanol (15 ml.) and water (3 ml.) was heated under reflux for four hours and then allowed to stand at room temperature for 7 days. Ethanol was then removed in vacuo, the residue was mixed with a dilute $NaHCO_3$ solution and filtered to remove 0.076 g., (m.p. 154°-156°C) of a colorless solid. Evaporation of the mother-liquors left a colorless solid, which was extracted separately with hot $CH_2Cl_2$ and filtered. Evaporation of the filtrate left a nearly colorless gum (0.497 g.) which was dissolved in absolute ethanol (5 ml.) and treated with hydrogen chloride by impinging a stream of dry HCl gas on the surface of the liquid. After refrigeration overnight, the crystals were filtered off, washed with cold (=5°C) ethanol and dried. The weight of the colorless solid was 0.344 g. (m.p. 240°C, decomposed). Infra-red and elemental analysis of a sample of the solid were used to determine the empirical formula of the solid to be $C_{14}H_{19}N_2OCl$.

exo-3-Dimethylaminomethylbenzonorbornen-2-one oxime hydrochloride, thus prepared, (0.719 g.) was converted to the free base (0.603 g.), which was obtained as a brownish gum. A solution of this material in dry absolute ethanol (35 ml.; dried over molecular sieves) was gradually treated with sodium wire (3.5 g.) under nitrogen. Towards the end of the addition, approximately 2 hours, more dry ethanol (10 ml.) was added and the solution stirred and heated. When all of the sodium had dissolved, the solution was evaporated to dryness in vacuo, and the colorless residual solid treated with water and $CH_2Cl_2$. The aqueous layer was drawn off and the organic layer, after drying over $Na_2SO_4$, was evaporated to dryness in vacuo to leave a brown oil (0.564 g.).

For the preparation of the hydrochloride, the above oil (0.55 g.) was dissolved in absolute ethanol (5 ml.) and dry HCl gas was impinged on the surface of the solution. After removal of solvent in vacuo at room temperature, the residual yellow froth was crystallized from ethanol (5 ml.)/ether (10 ml.). The collected solid which was beige in color weighed 0.628 g. (m.p. 274°–276°C, decomposed). The beige solid was analyzed by infra-red, nuclear magnetic resonance and elemental analysis techniques, and was determined to be the 1,2,3,4-tetrahydro-1,4-methanonaphthalen-exo-3-dimethylaminomethyl-endo-2-amine dihydrochloride, $C_{14}H_{22}Cl_2N_2$.

EXAMPLE 4

Preparation of 1,2,3,4-tetrahydro-1,4-methanonaphthalen-endo-3-methyl-endo-2-amine (IV).

exo-3-Dimethylaminomethylbenzonorbornen-2-one hydrochloride, prepared previously, (5 g.) was placed in a round bottom flask fitted with an air condenser and was heated in an oil bath maintained at 250°C. The melt was heated for several minutes and was then cooled and worked up with water and $CHCl_3$. The dark organic phase was treated with charcoal, filtered and evaporated to give a brown oil. Chromatography on Silicar CC7 using benzene as eluant gave a colorless oil (1.9 g., 40%).

The 3-methylenebenzonorbornen-2-one, thus prepared, (1.9 g.) was dissolved in ethyl acetate (100 ml.) with 10% Pd/C catalyst (300 mg.). Hydrogenation was performed on the Parr apparatus and was complete in 10 minutes. Shaking under hydrogen atmosphere was continued for a subsequent 20 minutes. The solution was filtered and evaporated to give a colorless oil (1.8 g., 95%).

The endo-3-methylbenzonorbornen-2-one, thus prepared, (1.8 g.) was dissolved in ethanol (7 ml.) and to this was added a solution containing hydroxylamine hydrochloride (1 g.) and sodium acetate (1.2 g.) in water (5 ml.). The mixture was heated on the steam bath for 1 hour and then allowed to stand at room temperature over 2 days. The reaction was worked up with chloroform and water. Evaporation of the dried organic layer gave white crystals (1.1 g.). Crystallization from hexane-benzene gave an analytical sample (m.p. 126°–128°C).

The endo-3-methylbenzonorbornen-2-one oxime, thus prepared, (1.0 g.) was dissolved in absolute alcohol (60 ml.) and sodium wire (6.0 g.) was added at such a rate as to maintain a gentle reflux. The mixture was heated for a short while at the end of the reaction to insure completion. The product was isolated after work-up with water and benzene. This crude material was dissolved in absolute ethanol and HCl gas was impinged on the surface of the solution. Evaporation of solvents gave a white solid, which was crystallized from ethanol/ether to give feathery crystals (m.p. 300°C).

The feathery crystals were analyzed by infra-red and elemental analysis techniques, and were determined to be the 1,2,3,4-tetrahydro-1,4-methanonaphthalen-endo-3-methyl-endo-2-amine hydrochloride, $C_{12}H_{16}ClN$.

EXAMPLE 5

Preparation of 1,2,3,4-tetrahydro-1,4-methanonaphthalen-exo-3-endo-2-diamine (V).

Norborn-5-ene-trans-2,3-dicarboxylic acid (10 g.) was heated at 150°C with 5,5-dimethoxytetrachlorocyclopentadiene (40 g.) for 7 hours. After cooling, the gum was stirred with benzene/hexane to give a crystalline solid (13.8 g.). Crystallization from methanol/water gave colorless crystals (m.p. 253.5°–255°C). A sample of the colorless crystals was analyzed using infra-red and elemental analysis techniques, and the empirical formula of the material was determined to be $C_{16}H_{16}Cl_4O_6$.

The Diels-Alder adduct, thus prepared, (33.8 g.) was stirred with concentrated $H_2SO_4$ (135 ml.) at room temperature for 1 hour. The mixture was then poured on ice, keeping the temperature as low as possible. After dilution with ice water to 1200 ml., the mixture was extracted with ether. The ether was dried and evaporated to give a white foam (29.2 g.) which was characterized by infra-red analysis only.

The 5,6,7,8-tetrachloro-9-keto-1,2,3,4,5,5a,8,8a-octahydro-1,4:5,8-dimethanonaphthalene-trans-2,3-dicarboxylic acid, thus prepared, (29.2 g.) was treated with o-dichlorobenzene (280 ml.) and heated under reflux for 2 hours. The resulting insoluble white powder was collected by filtration and washed with benzene and dried (14.2 g.). Recrystallization from methanol/water gave colorless needles (m.p. >300°C). The colorless needles were analyzed using infra-red, ultra-violet and elemental analysis techniques, and the empirical formula of the material was determined to be $C_{13}H_{10}Cl_4O_4$.

The 5,6,7,8-tetrachloro-1,2,3,4,5A,8a-hexahydro-1,4-methanonaphthalene-trans-2,3-dicarboxylic acid, thus prepared, (20 g.) was suspended in acetic acid (300 ml.) and bromine (7 ml.) was added. The mixture was heated at reflux with vigorous mechanical stirring, under nitrogen. After heating at reflux for 5 hours, the reaction was worked up by evaporation of the acetic acid. The product was recrystallized from acetic acid to give colorless crystals (12.5 g.; m.p. 297°–99°C), which were also characterized by infra-red analysis.

The 5,6,7,8-tetrachloro-1,2,3,4-tetrahydro-1,4-methanonaphthalene-trans-2,3-dicarboxylic acid, thus prepared, (6 g.) was dissolved in aqueous KOH (40 g. in 400 ml.) with shaking and heated on the steam bath. Raney nickel/aluminum alloy (25 g.) was added at such a rate as to control foaming, and after complete addition the mixture was allowed to stand on the steam bath, with occasional shaking, for 5 hours. The mixture was filtered, and then strongly acidified with concentrated HCl and extracted with ether. The ether extracts were combined, washed with water, saturated NaCl solution, and then dried over MgSO$_4$. Evaporation gave a white solid (3.4 g.) which was recrystallized from CHCl$_3$ to give colorless crystals (m.p. 238°–40°C), which were characterized by infra-red analysis, and after a methylation step using CH$_2$N$_2$, by nuclear magnetic resonance analysis.

The 1,2,3,4-tetrahydro-1,4-methanonaphthalene-trans-2,3-dicarboxylic acid, thus produced, (3.4 g.) was dissolved in water (3 g.) and acetone (20 ml.). The solution was cooled to 0°C in an ice/salt bath and triethylamine (8 g.) in acetone (80 ml.) was added and the resulting solution again cooled to 0°C, whereupon ethyl chloroformate (9 g.) in acetone (20 ml.) was added, keeping the temperature below 4°C. The mixture was stirred at 0°C for 30 minutes. To the mixture was cautiously added a solution of sodium azide (6.3 g.) in a minimum volume of water, again maintaining the temperature below 4°C, and stirring continued for a subsequent 90 minutes. The mixture was worked up with CHCl$_3$ and water to give the azide as a mobile oil, which was characterized as such by infra-red analysis. The azide was dissolved in toluene (80 ml.) and added dropwise to a flask heated on the steam bath. Vigorous gas evolution ensued. Heating was maintained for 60 minutes, then the toluene was removed under reduced pressure. It was immediately replaced by 20% HCl (40 ml.) and the mixture was heated for 1 hour. The solvents were removed after standing overnight at room temperature and the residue crystallized from EtOH/Et$_2$O to give shiny white crystals (1.7 g.) of 1,2,3,4-tetrahydro-1,4-methanonaphthalen-exo-3-endo-2-diamine dihydrochloride, C$_{11}$H$_{16}$Cl$_2$N$_2$, which was characterized as such by a determination of its melting point (>300°C) and by infra-red analysis.

EXAMPLE 6

Preparation of 1,2,3,4-tetrahydro-1,4-methanonaphthalen-exo-3-phenyl-endo-2-amine (VI).

exo-3-Phenylnorborn-5-ene-endo-2-carboxylic acid (5 g.) was mixed with 5,5-dimethoxytetrachlorocyclopentadiene (25 g.) and heated on the steam bath to give a homogeneous solution. The reaction was then heated at 160°C for 6 hours, and then allowed to cool. Hexane was added and the mixture placed under refrigeration. The product (8.5 g.) was collected by filtration and recrystallized from MeOH. The product was characterized by its melting point (208°–10°C) and by infra-red analysis.

The preparations of the 5,6,7,8-tetrachloro-9-keto-1,2,3,4,5,5a,8,8a-octahydro-1,4:5,8-dimethanonaphthalene-exo-3-phenyl-endo-2-carboxylic acid, and the 5,6,7,8-tetrachloro-1,2,3,4,5a,8a-hexahydro-1,4-methanonaphthalene-exo-3-phenyl-endo-2-carboxylic acid are analogous to the corresponding preparative steps described above for the preparation of 1,2,3,4-tetrahydro-1,4-methanonaphthalen-exo-3-endo-2-diamine di-hydrochloride.

Having thus prepared the 5,6,7,8-tetrachloro-1,2,3,4,5a,8a-hexahydro-1,4-methanonaphthalene-exo-3-phenyl-endo-2-carboxylic acid, a portion (10 g.) was suspended in acetic acid (240 ml.) and bromine (4 ml.) was added, and the mixture was brought to reflux. Heating was continued for 9 hours after which the mixture was cooled and the solvents were removed by a rotary evaporator to give a mobile liquid product (18 g.). Hexane/benzene was added, and the mixture was placed in a refrigerator to crystallize. The resulting 5,6,7,8-tetrachloro-1,2,3,4-tetrahydro-1,4-methanonaphthalene-exo-3-phenyl-endo-2-carboxylic acid (6.7 g.) was characterized by melting point (176°–78°C) and by infra-red analysis.

The tetrachloro acid prepared by the above procedure was dissolved in 10% KOH (530 ml.); it was also necessary to add methanol (100 ml.) to obtain a clear solution. This was heated on the steam bath and Raney nickel alloy (33.5 g.) was cautiously added, with shaking, at such a rate as to control foaming. The mixture was allowed to stand on the steam bath for approximately 4 hours, filtered to remove solids and finally strongly acidified with concentrated HCl. The acidified mixture was extracted with ether, the organic layers combined, washed with water, dried and finally evaporated to give the product (4.6 g.) as a white solid. A portion was crystallized from benzene/hexane to give beautiful needles. A sample of the needles (m.p. 154°–6°C) was analyzed using infra-red, nuclear magnetic resonance and elemental analysis techniques and the crystalline solid was determined to be 1,2,3,4-tetrahydro-1,4-methanonaphthalene-exo-3-phenyl-endo-2-carboxylic acid, C$_{18}$H$_{16}$O$_2$.

The acid from the previous reaction (3.0 g.) was suspended in water (2.0 g.) and acetone added to effect solution. This was cooled to 0°C, and triethylamine (1.35 g.) in acetone (23 ml.) was added, followed by ethyl chloroformate (1.65 g.) in acetone (5.9 ml.), at such a rate as to keep the temperature below 4°C. The mixture was stirred at 0°C for 30 minutes, then sodium azide (1.14 g.) in water (4 ml.) was slowly added, again keeping the reaction temperature below 4°C. This mixture was stirred at 0°C for 90 minutes and then worked up with CHCl$_3$ and water to give the azide, which was dissolved in toluene (60 ml.) and added dropwise to a flask heated on the steam bath. After complete addition, the solution was heated for 60 minutes. The toluene was removed under reduced pressure, then replaced by 20% HCl (40 ml.) and heated until gas evolution ceased. The solvents were removed, giving a beige powder (2.9 g.) which was crystallized from EtOH/Et$_2$O to give a white crystalline product. The 1,2,3,4-tetrahydro-1,4-methanonaphthalen-exo-3-phenyl-endo-2-amine hydrochloride (m.p. 254°–56°C), C$_{17}$H$_{18}$ClN, thus produced was characterized as such by infra-red analysis.

EXAMPLE 7

Preparation of 1,2,3,4-tetrahydro-1,4-ethanonaphthalen-exo-3-endo-2-diamine (VII).

2-Naphthol (10 g.) and maleic anhydride (9 g.) were heated for 35 minutes in an oil bath maintained at about 230°C. After cooling, ethyl acetate (40 ml.) was added and crystallization induced by scraping. Filtration gave the crude product (9.9 g., 59%) which melted at approximately 160°C. Careful fractional recrystallization gave two isomers, m.p. 194°–95°C and 193°–195°C, mixed m.p. approximately 160°C. The solvents used in this operation were benzene-acetone. The mixture of isomers was analyzed by infra-red and nuclear magnetic analysis techniques. Although the mixture of exo and endo isomers of benzobicyclo[2.2.2]octen-5-keto-2,3-dicarboxylic anhydride, thus produced may be separated by careful fractional crystallization, the initial mixture of isomers is quite suitable for use in the reaction scheme described below.

This mixture of anhydrides (13.3 g.) was dissolved in diethylene glycol (250 ml.) containing KOH (32.8 g.) and water to assist solution (10 ml.). Hydrazine hydrate (23 ml.) was added and the solution was heated at reflux for 10 minutes. The condenser was removed from the reaction flask and the temperature was raised to 190°C and maintained at this point for 6 hours. After cooling, the mixture was poured into a large volume of water, washed several times with ether and then strongly acidified with HCl. The product was extracted with ether and crystallized from ethyl acetate-benzene. The benzobicyclo[2.2.2]octene-endo-2-exo-3-dicarboxylic acid (12.8 g, 95% yield) was characterized by melting point (198°–99°C) and infra-red analysis. [See: K. Takeda et al, Chem. Ber., 95, 2344 (1962) and previous papers in this series].

The dicarboxylic acid, produced above, (6.1 g.) was suspended in water (8 ml.) and sufficient acetone was added to effect solution. The mixture was cooled to 2°C and triethylamine (5 g. in 50 ml. of acetone) was added. Keeping the temperature at 2°C, ethyl chloroformate (7.5 g. in 20 ml. of acetone) was added with constant stirring; during this time a voluminous precipitate was obtained. After stirring for a subsequent 30 minutes, sodium azide (4.5 g. in 15 ml. of water) was added at 2°C and stirring was maintained for 90 minutes. The mixture was poured into ice water and extracted with toluene. An aliquot of this solution showed mainly di-acid azide on infra-red analysis. After drying, the toluene solution was added dropwise to a flask heated on the steam bath and, after complete addition, heated for an hour. Evaporation of the toluene gave a pale yellow oil (6.4 g.; 100%) which was determined to be benzobicyclo[2.2.2]octene-endo-2-exo-3-diisocyanate. This material was not further characterized, but was used as such.

The diisocyanate from the above reaction (1.2 g.) was treated with 20% HCl (10 ml.) and heated briefly on the steam bath. The reaction was worked up by filtration, followed by addition of base to pH 11. Extraction with $CHCl_3$ was followed by evaporation of the organic solvents, and gave an oil, which was converted to the dihydrochloride by first dissolving in MeOH then adding concentrated HCl. After standing at room temperature overnight, a crystalline precipitate was obtained and collected by filtration to provide 320 mg (30% yield). A sample of the precipitate was characterized by melting point (>300°C) and by infra-red analysis, and was determined to be 1,2,3,4-tetrahydro-1,4-ethanonaphthalen-exo-3-endo-2-diamine dihydrochloride, $C_{12}H_{18}Cl_2N$.

ANTIVIRAL ACTIVITY

A significant aspect of the instant invention resides in the discovery that benzonorbornene derivatives of the class described having an amino substituent in the 2-endo configuration of the molecule and particularly those derivatives having 2-endo amino and 3-exo substituents, exhibit enhanced activity as opposed to corresponding analogous compounds having other configurations.

As an example, the 1,2,3,4-tetrahydro-1,4-methanonaphthalen-endo-2-amine, one of the active antiviral compounds disclosed herein, when used in in vivo testing on mice infected with fatal influenza (influenza $A_2$) showed 66% survival in mice treated with this compound, whereas almost no survival was observed in the control group. However, the isomer with the amino substituent taking up the exo configuration showed no antiviral activity by the same test procedure.

IN VITRO ACTIVITY OF ANTI-MYXOVIRUS COMPOUNDS

The in vitro activity of representative compounds of the present invention was determined as set forth below:

In preparing the compounds for testing, they were handled aseptically throughout. The compounds were dissolved in a minimum amount of a suitable solvent and the final dilutions were made up to the required volume in a complete culture medium used in assay and in concentration not exceeding the predetermined maximum non-toxic levels. All materials were tested first at three concentrations, and those which showed an inhibiting activity in that range were carefully retested at several concentrations below the maximum non-toxic levels.

The cell culture used in all primary in vitro anti-myxovirus assays was an established cell line of the human conjunctiva (G-2 cells). The cytotoxic studies of each of the compounds were performed prior to testing for antiviral activity to determine level of response of the cells to the potentially toxic action of the compounds. Cytotoxic levels were expressed as concentration which produces 50% inhibition of the cell growth ($CTD_{50}$) as compared to the appropriate controls, or as a maximal non-toxic concentration which does not produce any morphologically detectable inhibition of the cell growth ($CTD_0$).

Standard batches of virus were made by growing the virus in an appropriate cell culture, after passaging it on the chick embryo, and then making a pool which was dispersed in ampoules and kept frozen at $-76°C$ until used. The virus titer ($TCID_{50}$) was determined in the cell culture employed for the assays.

The cells were grown in test tubes in a suitable medium. Immediately before use the initial medium was replaced with the one containing the test compound in an appropriate concentration. After virus was added the infected culture was incubated at 32°C for a number of days. The medium was then drained, red blood cells added and after washing, the extent of hemadsorption evaluated. The percentage of inhibition of adsorption (a measure of antiviral activity) was then calculated.

In all anti-myxovirus testing in vitro, as well as in vivo, amantadine was used as a reference standard. It has been found that the most active compounds of this invention are those which exhibit the endo, exo configuration in the 2 and 3 positions respectively.

The results of in vitro tests compapred to Amantadine are shown in the following tables:

AMANTADINE HYDROCHLORIDE
Influenza $A_2$/Aichi/3/68, G-2 cells;

| Cytotoxicity $CTD_{50}$ $CTD_0$ (µg/ml) | Concentration of compounds (µg/ml) | % Inhibition | |
|---|---|---|---|
| | | 100 $TCID_{50}$ | 56.2 $TCID_{50}$ |
| >100 >100 | 100 | 43 | 87 |
| | 90 | 67 | 97 |
| | 80 | 27 | 70 |
| | 70 | 33 | 83 |
| | 60 | 0 | 53 |
| | 50 | 0 | 0 |
| | 40 | 0 | 0 |
| | 30 | 0 | 0 |

AMANTADINE HYDROCHLORIDE -continued
Influenza (swine), G-2 cells;

| Cytotoxicity $CTD_{50}$ $CTD_0$ ($\mu$g/ml) | Concentration of compounds ($\mu$g/ml) | % Inhibition | |
|---|---|---|---|
| | | 316 $TCID_{50}$ | 178 $TCID_{50}$ |
| >100 >100 | 100 | 100 | 100 |
| | 90 | 100 | 100 |
| | 80 | 100 | 100 |
| | 70 | 97 | 93 |
| | 60 | 83 | 90 |
| | 50 | 67 | 80 |
| | 40 | 10 | 17 |
| | 30 | 0 | 0 |

1,2,3,4-TETRAHYDRO-1,4-METHANONAPHTHALEN-ENDO-AMINE.HCl
Influenza $A_2$/Aichi/3/68 (human), G-2 cells;

| Cytotoxicity $CTD_{50}$ $CTD_0$ ($\mu$g/ml) | Concentration of compounds ($\mu$g/ml) | % Inhibition | |
|---|---|---|---|
| | | 178 $TCID_{50}$ | 17.8 $TCID_{50}$ |
| >100 >100 | 100 | 90 | 97 |
| | 90 | 80 | 97 |
| | 80 | 77 | 97 |
| | 70 | 53 | 90 |
| | 60 | 37 | 87 |
| | 50 | 10 | 30 |
| | 40 | 0 | 13 |
| | 30 | 0 | 0 |

Influenza (swine), G-2 cells;

| Cytotoxicity $CTD_{50}$ $CTD_0$ ($\mu$g/ml) | Concentration of compounds ($\mu$g/ml) | % Inhibition | |
|---|---|---|---|
| | | 316 $TCID_{50}$ | 178 $TCID_{50}$ |
| >100 >100 | 100 | 100 | 100 |
| | 90 | 97 | 100 |
| | 80 | 90 | 97 |
| | 70 | 70 | 93 |
| | 60 | 7 | 80 |
| | 50 | 0 | 7 |
| | 40 | 0 | 0 |

1,2,3,4-TETRAHYDRO-1,4-METHANONAPHTHALEN-EXO-3-DIMETHYLAMINOMETHYL-ENDO-2-AMINE.2HCl
Influenza $A_2$/Aichi/3/68 (human), G-2 cells;

| Cytotoxicity $CTD_{50}$ $CTD_0$ ($\mu$g/ml) | Concentration of compound ($\mu$g/ml) | % Inhibition |
|---|---|---|
| | | 100 $TCID_{50}$ |
| >100 >100 | 100 | 90 |
| | 66.7 | 87 |
| | 33.3 | 3 |

1,2,3,4-TETRAHYDRO-1,4-ETHANONAPHTHALEN-EXO-3-ENDO-2-DIAMINE.2HCl
Influenza $A_2$/Aichi/3/68 (human) G-2 cells;

| Cytotoxicity $CTD_{50}$ $CTD_0$ ($\mu$g/ml) | Concentration of compound ($\mu$g/ml) | % Inhibition | |
|---|---|---|---|
| | | 100 $TCID_{50}$ | 31.6 $TCID_{50}$ |
| >100 >100 | 100 | 83 | 100 |
| | 90 | 80 | 100 |
| | 80 | 60 | 100 |
| | 70 | 57 | 100 |
| | 60 | 80 | 100 |
| | 50 | 67 | 95 |
| | 40 | 30 | 87 |
| | 30 | 20 | 60 |
| | 20 | 0 | 7 |
| | 10 | 0 | 0 |

Influenza (swine), G-2 cells;

| Cytotoxicity $CTD_{50}$ $CTD_0$ ($\mu$g/ml) | Concentration of compound ($\mu$g/ml) | % Inhibition | |
|---|---|---|---|
| | | 316 $TCID_{50}$ | 10 $TCID_{50}$ |
| >100 >100 | 100 | 100 | 100 |
| | 80 | 100 | 100 |
| | 60 | 100 | 100 |
| | 50 | 100 | 100 |
| | 40 | 97 | 100 |
| | 30 | 90 | 100 |
| | 20 | 56 | 70 |
| | 10 | 0 | 0 |

The relative antiviral activity of representative compounds as a result of in vitro testing is shown as follows:

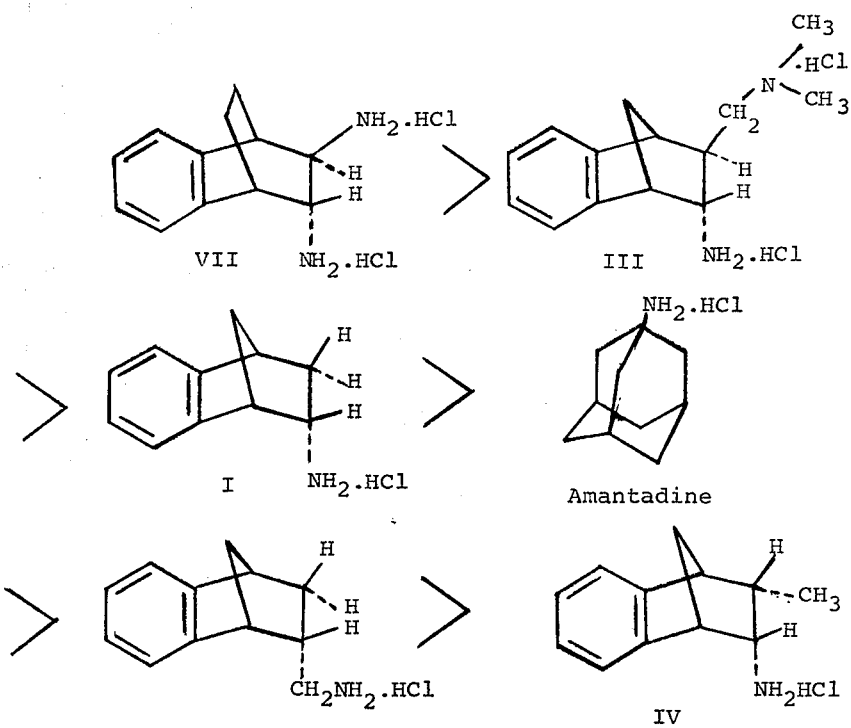

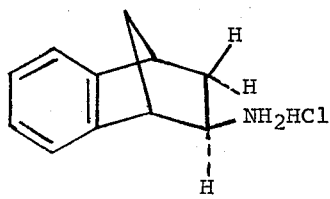

(Not Active)

As mentioned above, Amantadine is included as a reference point. In regard to the unexpected relatively low antiviral activity in the 1,2,3,4-tetrahydro-1,4-methanonaphthalen-endo-3-methyl-endo-2-amine, it is believed that the endo-3-methyl group has reduced the activity.

It is within the scope of the present invention to use the known analogs of the Compound VII as anti-influenza agents, i.e., compounds within the general formula where $R_3$ can be hydrogen and $R_4$ and $R_5$ can be hydrogen or methyl. Two of such compound 2-endo-methylamino-1,2,3,4-tetrahydro-1,4-ethanonaphthalene hydrochloride and 2-endo-dimethylamino-1,2,3,4-tetrahydroethanonaphthalene hydrochloride are disclosed in Japanese Patent No. 18,944 of 1966. However, their antiviral activity was not recognized by the patentees.

When the compounds of the instant invention are used as antiviral agents they may be employed alone or in combination with the usual pharmaceutically acceptable carriers which are discussed in detail in the aforementioned U.S. Pat. Nos. 3,483,254; 3,496,228; 3,538,160; 3,534,084; and 3,592,934. The proportion of the antiviral agent with respect to the carrier is determined by its solubility and chosen route of administration.

The antiviral compounds of this invention can be administered according to this invention by any means that effects contact of the active ingredient compound with the site of influenza viral infection in the body of the living host. It will be understood that this includes the site prior to infection setting in as well as after. For example, administration can be intranasally, orally, or parenterally, that is subcutaneously, intravenously, intramuscularly, or intraperitoneally. Activity against influenza virus $A_2$ by the latter route has been confirmed by tests in mice.

The following Table shows the toxicity of respresentative compounds I, III, and VII along with that of Amantadine.

| | TOXICITY OF IN VITRO ACTIVE ANTI-MYXOVIRUS COMPOUNDS IN MICE | |
|---|---|---|
| Animals: | Charles River white mice, 9–11 g. of starting weight, 6 mice per group. | |
| Amantadine and Compounds I, III and VII | *I/P route: | 100–125–150–175–200 mg/kg (Compound I) 150–175–200,225,250, 275–300–325 mg/kg (Aman.) 700–725–750–775–800 mg/kg (Compound VII) 100–250–500–750 mg/kg (Compound III) |
| | **P/O route: 200–225–250–275 (Compound I) Mice were weighed each day before administration of the drugs and doses adjusted according to the actual weight of individual animal. All drugs were dissolved in water and diluted to the proper concentration (e.g., 20% by weight) with the phosphate-buffered saline (PBS). | |

| Compound | Route of Administration | Maximal non-toxic dose $LD_0$ (mg/kg) | | 50% toxic dose $LD_{50}$ (mg/kg) | |
|---|---|---|---|---|---|
| | | Acute | Subacute | Acute | Subacute |
| Amantadine | I/P | 175 | 150 | 225 | 175–200 |
| Compound I | I/P | 125 | 100 | 100 | 100 |
| | P/O | 250 | 225 | 275 | 250–275 |
| Compound VII | I/P | 700 | 700 | 775–800 | 800 |
| Compound III | I/P | 500 | 250 | 750 | 500–750 |

*I/P - intraperitoneally
**P/O - oral

From the foregoing it will be seen that the maximum single dosage for compound I should be no greater than 100 mg/kg. Compounds VII and III were far less toxic than either the known antiviral agent Amantadine or compound I and can be used in larger maximum dosages.

virus infection. The results of some of these tests are summarized in the following table:

| Expt. | Virus Dose ($LD_{50}$) | Drug | Drug Dose (I/P, mg/kg) | Survival S/T** | % | Mean Survival Time* Days | Increase (Days) |
|---|---|---|---|---|---|---|---|
| 1 | 1.44 | Virus, only | 0 | 10/30 | 33.3 | 8.07 | 0 |
|  |  | Amantadine | 80 | 27/30 | 90.0 | 15.4 | 7.33 |
|  |  | Compound I | 80 | 26/30 | 86.7 | 15.4 | 7.33 |
| 2 | 2.24 | Virus, only | 0 | 4/27 | 14.8 | 12.2 | 0 |
|  |  | Amantadine | 100 | 26/27 | 96.3 | 14.9 | 2.7 |
|  |  | Compound I | 80 | 18/27 | 66.6 | 14.1 | 1.9 |
| 3 | 2.88 | Virus, only | 0 | 1/24 | 4.2 | 10.1 | 0 |
|  |  | Amantadine | 100 | 11/12 | 91.6 | 14.6 | 4.5 |
|  |  | Compound I | 100 | 8/12 | 66.4 | 13.8 | 3.1 |
| 4 | 3.80 | Virus, only | 0 | 1/30 | 3.3 |  | 0 |
|  |  | Amantadine | 100 | 12/30 | 39.6 |  |  |
|  |  | Compound VII | 100 | 6/30 | 19.8 |  |  |
|  |  | Compound III | 100 | 8/30 | 26.4 |  |  |

*Mean survival time (days) = number of mice alive each day (up to the last day of experiment) divided by total number of mice in group.
**T = Total number of animals infected
S = Number of surviving animals

IN VIVO ACTIVITY OF ANTI-MYXOVIRUS COMPOUNDS

In our experimental models for testing of anti-myxovirus activity mice were intranasally infected with mouse adapted human influenza $A_2$ virus in an amount to cause development of acute influenza resulting in death of animals. When animals so infected were treated with Amantadine (the reference "positive control" substance) or representative Compounds I, III or VII administered intraperitoneally, those compounds exhibited a significant antiviral effect against influenza virus infection.

These results indicate that the treatment of influenza $A_2$ infection in mice with the compounds of the invention produces a reduction in mortality under the experimental conditions chosen. They compare favorably with Amantadine which is one of the few compounds presently known which is generally accepted to be significantly active against influenza in vivo.

In the following experiment, compound I was tested at different levels for preventive control of influenza as follows:

| Animals: | Charles River white mice, starting weight: 10–12 g; 12 mice per group (24 mice as control). |
|---|---|
| Virus: | Mice were inoculated intranasally with influenza $A_2$ virus Aichi/2/68, with a titer of 2.88 $LD_{50}$, suspended in PBS. |
| Compound I: | Mice were divided into 5 groups and received respective doses of the drug: 100–85–70–55–40 mg/kg/day intraperitoneally, once a day for 16 days beginning one day prior to infection with the virus. Mice were weighed each day before inoculations and doses adjusted according to the actual weight of each animal. The active compound was suspended in phosphate buffered saline. |

The results are shown in the following tables:

|  | GROUP | DAYS POSTINFECTION / CUMULATIVE MORTALITY | | | | | | |
|---|---|---|---|---|---|---|---|---|
|  |  | 8 N/% | 9 N/% | 10 N/% | 11 N/% | 12 N/% | 13 N/% | 14 N/% |
|  | Control (virus only) | 2/8.3 | 11/45.8 | 17/70.8 | 21/87.5 | 21/87.5 | 23/95.8 | 23/95.8 |
|  | 100mg/kg | 0/0 | 0/0 | 2/16.7 | 3/25.0 | 4/33.3 | 4/33.3 | 4/33.3 |
| Compound I | 85mg/kg | 0/0 | 1/8.3 | 3/25.0 | 4/33.3 | 6/50.0 | 6/50.0 | 6/50.0 |
| + | 70mg/kg | 1/8.3 | 1/8.3 | 5/41.7 | 6/50.0 | 6/50.0 | 6/50.0 | 6/50.0 |
| Virus | 55mg/kg | 1/8.3 | 2/16.7 | 5/41.7 | 7/58.3 | 9/75.0 | 11/91.6 | 11/91.6 |
|  | 40mg/kg | 1/8.3 | 5/41.7 | 7/58.3 | 9/75.0 | 10/83.3 | 11/91.6 | 11/91.6 |

| Group | (dose) | Survivors S/T$^{(a)}$ | % | $p^{(b)}$ | Mean survival time Days | Increase (days) |
|---|---|---|---|---|---|---|
| Virus control | (2.9 $LD_{50}$) | 1/24 | 4.2 | — | 10.1 | 0 |
| Virus + CPD I | (100mg/kg) | 8/12 | 66.4 | 0.01 | 13.6 | 3.5 |
| Virus + CPD I | ( 85mg/kg) | 6/12 | 50.0 | 0.01 | 12.9 | 2.8 |
| Virus + CPD I | ( 70mg/kg) | 6/12 | 50.0 | 0.01 | 12.4 | 2.3 |
| Virus + CPD I | ( 55mg/kg) | 1/12 | 8.3 |  | 11.2 | 1.1 |
| Virus + CPD I | ( 40mg/kg) | 1/12 | 8.3 |  | 10.5 | 0.4 |

$^{(a)}$Total number of animals infected
$^{(b)}$Probability factor — less than 0.3 significant antiviral activity, less than 0.05 highly significant antiviral activity.

Similar results have been demonstrated with other compounds of the invention.

The compounds within the scope of this invention are valuable for influenza viral prophylaxis, as well as for therapeutic treatment.

In general, the compounds of this invention are most desirably administered at a concentration level that will afford effective results without causing any harmful or deleterious side effect in the subject being treated, i.e., in an effective, non-toxic amount. The dosage administered will also be dependent upon the virus being treated, the age, health and weight of the recipient, the extent of infection, kind of concurrent treatment if any, frequency of treatment, and the nature of the effect desired. For example, a daily dosage of 10 to 100 mg/kg of body weight of compound I dissolved or suspended in phosphate buffer solution (PBS) may be safely and effectively administered to mice by the intraperitoneal route. Similar or larger dosages of the related compounds III and VII may likewise be administered. Dosages are readily adjusted by known procedures for administration to other animal hosts including human and avian hosts.

The compounds of the present invention can be employed in dosage forms in combination with pharmaceutically acceptable carriers, solvents, diluents, and the like to provide liquid solutions or suspensions for intranasal or parenteral use.

In general, water, saline, aqueous dextrose (glucose) and related sugar solutions and glycols such as propylene glycol or polyethylene glycol are preferred liquid carriers, particularly for injectable solutions. Sterile injectable solutions such as buffered saline will ordinarily contain from about 0.5% to 25% by weight of the active ingredient.

It will be apparent from the foregoing descriptions that the 1,2,3,4-tetrahydro-1,4-alkanonaphthalenamine products of this invention and their acid salt derivatives constitute a valuable class of antiviral agents. One skilled in the art will also appreciate that the processes disclosed in the above examples are merely illustrative and are capable of wide variation and modification without departing from the spirit of this invention.

We claim:
1. A compound selected from the group consisting of 1,2,3,4-tetrahydro- 1,4-methanonaphthalen-exo-3-dimethylamino-methyl-endo-2-amine and its pharmaceutically acceptable acid addition salts.
2. A hydrochloride of the compound of claim 1.
3. A compound selected from the group consisting of 1,2,3,4-tetrahydro- 1,4-methanonaphthalen-exo-3-phenyl-endo-2-amine and its pharmaceutically acceptable acid addition salts.
4. The hydrochloride of the compound of claim 3.
5. A compound selected from the group consisting of 1,2,3,4-tetrahydro- 1,4-ethanonaphthalen-exo-3-endo-2-diamine and its pharmaceutically acceptable acid addition salts.

* * * * *

UNITED STATES PATENT OFFICE
CERTIFICATE OF CORRECTION

Patent No. 3,932,512    Dated January 13, 1976

Inventor(s) Kekhusroo R. Bharucha et al

It is certified that error appears in the above-identified patent and that said Letters Patent are hereby corrected as shown below:

On the cover page at [54], line 2, before "-ALKANO" insert ---4--- so that this line reads "1,2,3,4-TETRAHYDRO-1,4-ALKANO".

Column 1, line 1, in the title, before "-ALKANO" insert ---4--- so that this line reads "ANTIVIRAL 1,2,3,4-TETRAHYDRO-1,4-ALKANO".

Column 7, line 4, change the bold-face print of the first "2" to regular print.

Column 9, line 1, change "(=5°C)" to ---(-5°C)---.

Column 10, line 51, change "5A" to ---5a---.

Column 14, line 54, change "compapred" to ---compared---.

Signed and Sealed this twenty-seventh Day of April 1976

[SEAL]

Attest:

RUTH C. MASON
*Attesting Officer*

C. MARSHALL DANN
*Commissioner of Patents and Trademarks*